(12) United States Patent
van Praag et al.

(10) Patent No.: US 7,763,588 B2
(45) Date of Patent: Jul. 27, 2010

(54) METHOD FOR INCREASING COGNITIVE FUNCTION AND NEUROGENESIS

(75) Inventors: Henriette van Praag, San Diego, CA (US); Fred H. Gage, La Jolla, CA (US); John Hammerstone, Easton, PA (US); Mark Allen Kelm, East Stroudsburg, PA (US)

(73) Assignees: The Salk Institute for Biological Studies, La Jolla, CA (US); Mars, Incorporated, McLean, VA (US)

( * ) Notice: Subject to any disclaimer, the term of this patent is extended or adjusted under 35 U.S.C. 154(b) by 1557 days.

(21) Appl. No.: 10/866,049

(22) Filed: Jun. 10, 2004

(65) Prior Publication Data

US 2005/0004046 A1 Jan. 6, 2005

Related U.S. Application Data

(60) Provisional application No. 60/478,164, filed on Jun. 13, 2003.

(51) Int. Cl.
*A61K 31/7048* (2006.01)
*A61K 31/353* (2006.01)
*A61K 31/13* (2006.01)
*A61P 25/28* (2006.01)

(52) U.S. Cl. ............ 514/27; 514/456; 514/644
(58) Field of Classification Search .......... 514/27, 514/456, 644
See application file for complete search history.

(56) References Cited

U.S. PATENT DOCUMENTS

| | | | |
|---|---|---|---|
| 4,428,876 A | 1/1984 | Iwamura | |
| 5,702,752 A | 12/1997 | Gugger et al. | |
| 5,910,308 A * | 6/1999 | D'Jang | 424/729 |
| 5,922,756 A * | 7/1999 | Chan | 514/456 |
| 6,239,114 B1 * | 5/2001 | Guthrie et al. | 514/32 |
| 2002/0151506 A1 * | 10/2002 | Castillo et al. | 514/27 |
| 2003/0180406 A1 | 9/2003 | Sies | |

FOREIGN PATENT DOCUMENTS

EP 0842660 A1 * 5/1998

OTHER PUBLICATIONS

Socci et al., "Chronic antioxidant treatment improves the cognitive performance of aged rats", Brain Research, 693, 1995, pp. 88-94.*
Spencer et al., Epicatechin and its in vivo metabolite, -O-methyl epicatechin, protect human fibroblasts from oxidative-stress-induced cell death involving caspase-3 activation, Biochem J, (2001) 354, 493-500 (Printed in Great Britain).*
Allen et al., "Ataxia telangiectasia mutated is essential during adult neurogenesis," *Genes & Development.* 15:554-566 (2001).
Bohme et al., "Altered synaptic plasticity and memory formation in nitric oxide synthase inhibitor-treated rats," *Procl. Natl. Acad. Sci. USA*, 90:9191-9194 (1993).
Dinges et al., "Cumulative Sleepiness, Mood Disturbance, and Psychomotor Vigilance Performance Decrements During a Week of Sleep Restricted to 4-5 Hours per Night," *Sleep*, 20(4):267-277 (1997).
Morris, J., "Developments of a water-maze procedure for studying spatial learning in the rat," *Neurosci. Methods*, 11:47-60 (1984).
Newhouse et al., "The Effects of d-Amphetamine on Arousal, Cognition, and Mood After Prolonged Total Sleep Deprivation," *Neuropsychopharmacology*, 2(2):153-164 (1989).
Newhouse et al., "Stimulant Drug Effects on Performance and Behavior After Prolonged Sleep Deprivation: A comparison of Amphetamine, Nicotine, and Deprenyl," *Military Psychology*, 4(4):207-233 (1992).
Ohayon et al., "Daytime Sleepiness and Cognitive Impairment in the Elderly Population," *Arch Intern Med.*, 162:201-208 (Jan. 2002).
Rhodes et al., "Exercise Increases Hippocampal Neurogenesis to High Levels but Does Not Improve Spatial Leaning in Mice Bred for Increased Voluntary Wheel Running," *Behavioral Neuroscience*, 117(5):1006-1016 (Oct. 2003).
Thorne et al., "Plumbing Human Performance Limits During 72 Hours of High Task Load," *Military Systems*, Defense and Civil Institute of Environmental Medicine, Toronto, (1983).
van Praag et al., "Running enhances neurogenesis, learning, and long-term potentiation in mice," *Procl. Natl. Acad. Sci. USA*, 96(23):13427-13431 (1999).
van Praag et al., "Functional neurogenesis in the adult hippocampus," *Nature*, 415:1030-1034 (Feb. 2002).
Zhu et al., "Expression of Inducible Nitric Oxide Synthase after Focal Cerebral Ischemia Stimulates Neurogenesis in the Adult Rodent Dentate Gyrus," *J. Neurosci.*, 23(1):223-229, (Jan. 2003).
van Praag et al., "Plant-Derived Flavanol (−) Epicatechin Enhances Angiogenesis and Retention of Spatial Memory in Mice," *J. Neurosci.* 27:5869-5878, 2007.
van Praag, "Exercise and the Brain: Something to Chew on," *Trends Neurosci.* 32:283-290, 2009.

* cited by examiner

*Primary Examiner*—Sreeni Padmanabhan
*Assistant Examiner*—Sahar Javanmard
(74) *Attorney, Agent, or Firm*—Klarquist Sparkman, LLP

(57) ABSTRACT

The invention provides a method for improving cognitive performance in a physically active subject. The invention further provides a method of enhancing neurogenesis in a physically active subject. In one embodiment, the method encompasses administering to the subject an effective amount of one or more flavonoids. In a further embodiment, the method encompasses administering to the subject an effective amount of one or more antioxidants.

43 Claims, 6 Drawing Sheets

METHOD FOR INCREASING COGNITIVE FUNCTION AND NEUROGENESIS

This application is based on, and claims the benefit of, U.S. Provisional Application No. 60/478,164, filed Jun. 13, 2003, and entitled METHOD FOR INCREASING COGNITIVE FUNCTION AND NEUROGENESIS, and which is incorporated herein by reference.

This invention was made with government support under grant number DAAD 19-02-1-0267 awarded by the Defense Advanced Research Projects Agency (DARPA), an organization of the Department of Defense. The government may have rights in aspects of this invention.

BACKGROUND OF THE INVENTION

The present invention relates generally to neurobiology and behavioral biology and more specifically to methods for increasing cognitive function.

A variety of factors, such as sleep deprivation aging and certain neurodegenerative diseases, can have adverse effects on cognitive performance. Recent research shows that exercise can counteract the detrimental effects of these conditions on memory function. Physical activity has been shown to improve spatial learning in rodents. In addition, physical activity increased synaptic plasticity in the adult rodent hippocampus, a brain area important for learning and memory, using long-term potentiation as an electrophysiological model of learning and memory.

Enhanced learning and synaptic plasticity are correlated with an increase in new nerve cells in the dentate gyrus of the hippocampus, one of the few brain areas where new neurons are generated in adult mammals, including humans. Although the functional significance of new neurons in the adult brain is not clear, enhanced production of new cells has been associated with improved learning and vice versa. The molecular mechanisms underlying neurogenesis remain largely unknown and effective therapies are not currently available to improve neurodegeneration and the decrease in cognitive impairment that is associated with neuronal degeneration.

Thus, there exists a need for compounds and methods that enhance neurogenesis and improve cognitive performance including memory and learning in mammals. The present invention satisfies this need and provides related advantages as well.

SUMMARY OF THE INVENTION

Figure 1A:
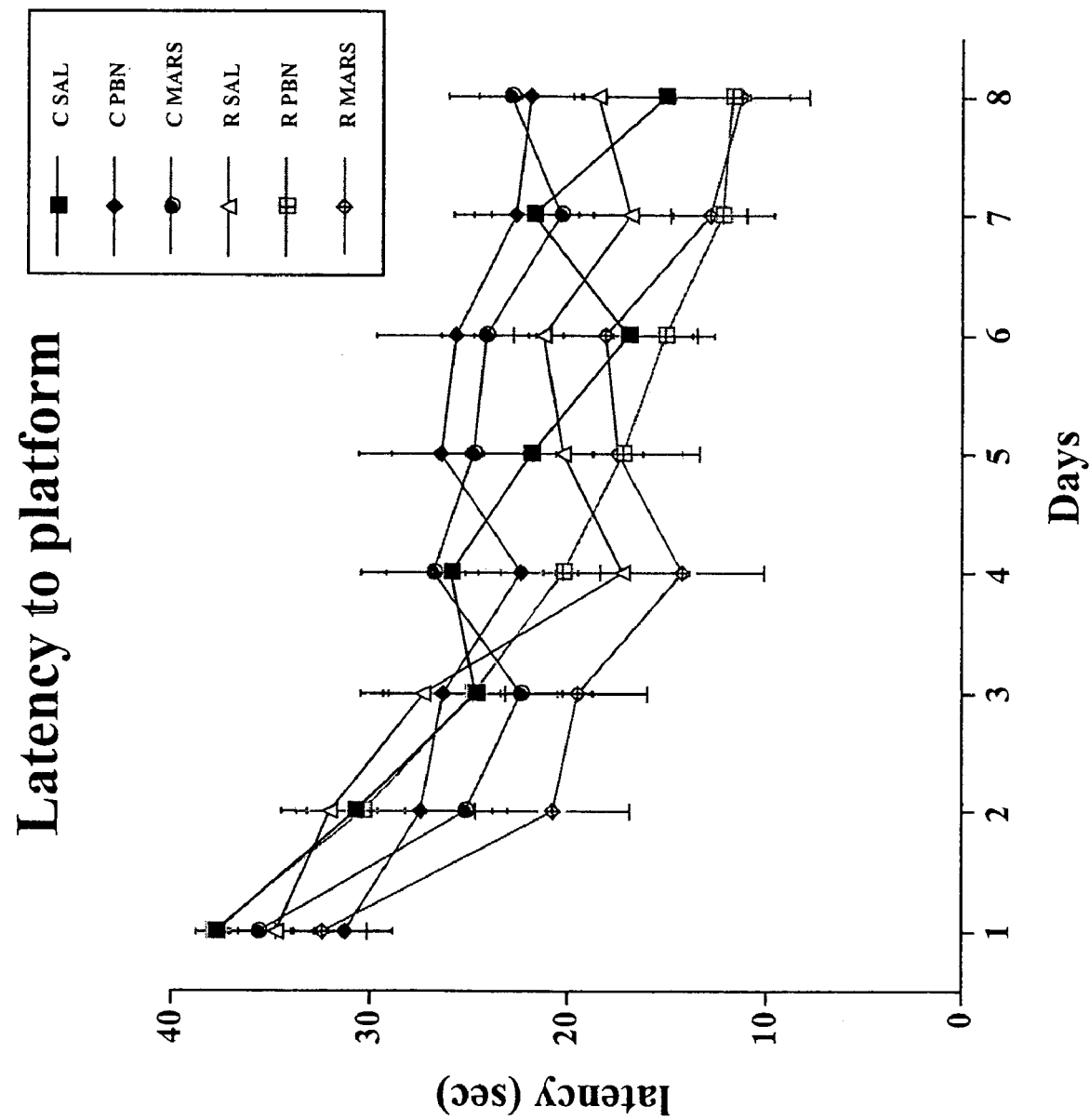
FIG. 1 summarizes the water maze learning studies for the following groups: Control/Saline (CS) Control/PBN (CP), Control/Mars (CM), Runner/Saline (RS), Runner/PBN (RP) and Runner/Mars (RM). Panel A shows the differences between groups in latency to platform. Panel B shows the differences between the groups in swim speed. Panel C shows the differences between the groups in path length.

The invention provides a method for improving cognitive performance in a subject that is physically active. The invention further provides a method of enhancing neurogenesis in a subject that is physically active.

In one embodiment, the method for improving cognitive performance encompasses administering to a physically active subject an effective amount of one or more flavonoids. In this embodiment, the one or more flavonoids include 3'-methylated epicatechin. The one or more flavonoids can also include 4'-methylated epicatechin. The one or more flavonoids can also encompass both 3'-methylated epicatechin and 4'-methylated epicatechin, which can be administered in equal amounts. In a further embodiment, the method for improving cognitive performance encompasses administering to a physically active subject an effective amount of one or more antioxidants. The one or more antioxidants administered to a physically active subject in this embodiment of the invention can comprise N-tert-Butyl-phenylnitrone (PBN).

The invention also provides a method for enhancing neurogenesis encompasses administering to a physically active subject an effective amount of one or more flavonoids. In this embodiment, the one or more flavonoids include 3'-methylated epicatechin. The one or more flavonoids can also include 4'-methylated epicatechin. The one or more flavonoids can also encompass both 3'-methylated epicatechin and 4'-methylated epicatechin, which can be administered in equal amounts. In a further embodiment, the method for enhancing neurogenesis encompasses administering to a physically active subject an effective amount of one or more antioxidants. The one or more antioxidants administered to a physically active subject in this embodiment of the invention can comprise N-tert-Butyl-phenylnitrone (PBN).

DETAILED DESCRIPTION OF THE INVENTION

The present invention provides a method for improving cognitive performance in a physically active subject. The invention further provides a method of enhancing neurogenesis in physically active subject. In one embodiment, the method encompasses administering to the subject an effective amount of one or more flavonoids. In a further embodiment, the method encompasses administering to the subject an effective amount of one or more antioxidants.

The invention is based, in part, on the unexpected discovery of a synergistic action between physical exercise and administration of either a flavonoid or an antioxidant. While administration of either compound does not affect cognitive performance or neurogenesis under basal conditions, the invention described herein discloses that, when combined with a physical activity, for example, a physical exercise routine either a flavonoid or an antioxidant can increase cognitive performance and enhance cell proliferation, in particular, neurogenesis. As further disclosed herein, the method of the invention also can be used to increase cell survival in a physically active subject.

In one embodiment of the invention, the one or more flavonoids include catechins or flavonols, for example, 3'-methylated epicatechin. The one or more flavonoids can also include the flavonoid designated 4'-methylated epicatechin. In another embodiment described herein, the one or more flavonoids encompass both 3'-methylated epicatechin and 4'-methylated epicatechin. In this embodiment, the 3'- and 4'-methylated epicatechin can be administered in equal amounts (1:1) or any other ratio desired by the user, for example, 1:2, 1:3, 1:4, 1:5, 1:6, 1:7, 1:8, 1:9, 1:10.

In addition to flavonols and catechins, the invention method also is contemplated to be practiced with compounds of other flavonoid subclasses. Flavonoids comprise the most common group of plant polyphenols and provide much of the flavor and colour to fruits and vegetables. More than 5000 different flavonoids have been described. The six major subclasses of flavonoids include the flavones, including apigenin, luteolin; flavonols, including quercetin and myricetin; flavanones, including naringenin and hesperidin; catechins or flavonols, including epicatechin and gallocatechin; anthocyanidin, including cyanidin and pelargonidin; and isoflavones, including genistein and daidzein. Most of the flavonoids present in plants are attached to sugars (glycosides), although occasionally they are found as aglycones. While exemplified herein with the catechins, practice of the disclosed invention with members of all subclasses and their derivatives is contemplated.

Catechin and its gallate are major ingredients in green tea and have anti-oxidant, cancer preventive, vitamin P, antimicrobial and radio protective effects. Oxidative and nitrosative stress is associated with the pathology of neurodegeneration and aging. The molecular mechanisms underlying oxidative/nitrosative stress-induced neuronal damage involve a mode of death in which mitogen-activated protein kinase (MAPK) signaling pathways are implicated. Therefore, a compound that is administered to a physically active subject, for example, a subject undergoing a physical exercise routine, can be a modulator of a MAPK signaling pathway.

As exemplified herein, 3'- and 4'-methylated epicatechin can be administered in equal amounts (1:1) to a physically active subject, for example, a subject undergoing a physical exercise routine, to improve cognitive performance and increase neurogenesis. Similarly, one or more antioxidants can be administered to a physically active subject, for example, a subject undergoing a physical exercise routine, to improve cognitive performance and increase neurogenesis.

Nitric oxide synthase (NOS) plays a role in memory, learning and hippocampal neurogenesis as described by Bohme et al., *Procl. Natl. Acad. Sci. USA*, 90(19): 9191-9194 (1993); and Zhu et al., *J. Neurosci.* 23(1): 223-229 (2003), both of which are incorporated herein by reference in their entirety. The 3'- and 4'-methylated epicatechin compound can modulate nitric oxide synthase (NOS), endothelial function and blood flow, including cerebral blood flow. Excessive glutamate receptor stimulation, in particular NMDA receptor activation, can lead to stimulation of NOS, the enzyme responsible for the formation of NO. Nitric oxide mediates many of the effects of NMDA, including neurotransmitter release from striatum and cerebral cortex. In addition to formation of nitric oxide, itself a free radical, NMDA receptor activation can lead to the generation of other free radical species. Treatment with free radical scavengers, such as N-tert-Butyl-phenylnitrone (PBN), can prevent NMDA-induced neurotoxicity and protect against neuronal damage in a variety of in vitro and in vivo models. As exemplified herein with the flavonoids, 3'- and 4'-methylated epicatechin and the anti-oxidant PBN, the method provided by the invention also can be practiced by administering a modulator of NOS.

As described herein, the invention also is directed to a method for improving cognitive performance in a physically active subject, for example, a subject undergoing a physical exercise routine, by administering to the subject one or more antioxidants. The invention further provides a method of enhancing neurogenesis in a physically active subject, for example, a subject undergoing a physical exercise routine, by administering to the subject one or more antioxidants. As exemplified below with N-tert-Butyl-phenylnitrone (PBN), the invention methods can be practiced by administering one or more antioxidants to a physically active subject, for example, a subject undergoing a physical exercise routine. In a further embodiment, the invention methods can be practiced by administering one or more non-flavonoid antioxidants in combination with one or more flavonoids to a physically active subject, for example, a subject undergoing a physical exercise routine.

Generation of reactive oxygen species (ROS) is characteristic for hypoxia and especially for reoxygenation. Of the ROS, hydrogen peroxide and superoxide are both produced in a number of cellular reactions, including the iron-catalysed Fenton reaction, and by various enzymes such as lipoxygenases, peroxidases, NADPH oxidase and xanthine oxidase. The main cellular components susceptible to damage by free radicals are lipids (peroxidation of unsaturated fatty acids in membranes), proteins (denaturation), carbohydrates and nucleic acids. Consequences of hypoxia-induced oxidative stress depend on tissue and/or species (i.e. their tolerance to anoxia), on membrane properties, on endogenous antioxidant content and on the ability to induce the response in the antioxidant system. Effective utilization of energy resources (starch, sugars) and the switch to anaerobic metabolism and the preservation of the redox status of the cell are vital for survival. The formation of ROS is prevented by an antioxidant system that consists of low molecular mass antioxidants (ascorbic acid, glutathione, tocopherols), enzymes regenerating the reduced forms of antioxidants, and ROS-interacting enzymes such as SOD, peroxidases and catalases. In plant tissues, many phenolic compounds, in addition to tocopherols, serve as antioxidants, including flavonoids as described above, tannins and lignin precursors can work as ROS-scavenging compounds. Antioxidants act as a cooperative network, employing a series of redox reactions. Interactions between ascorbic acid and glutathione, and ascorbic acid and phenolic compounds are well known. All of these antioxidants are contemplated for practicing the invention methods.

As used herein the term "subject" refers to a mammal, such as a mouse, guinea pig, rat, dog or human. It is understood that the preferred subject is a human.

The methods provided by the present invention are useful for the treatment of any condition that is associated with an impairment in cognitive performance. As used herein, the phrase "cognitive performance" refers to mental functions including, for example, learning, problem solving, remote memory, recent memory, word comprehension, orientation, attention span, calculation, abstract thinking, and judgment. As described below, there are various tests known to those having skill in this art for determining whether a compound improves cognitive performance in a subject. Representative examples of such tests include ADAS, MMSE, CIBIC and Global Deterioration.

Conditions associated with a decrease in cognitive performance include aging, Alzheimer's disease, Pick's disease, seizures, neurodegenerative illnesses, dementia, head trauma or injury, hysteria accompanied by confusion, seizures, effects of general anesthetics such as halothane, isoflurane, and fentanyl, alcoholism, stroke or transient ischemic attack (TIA), transient global amnesia, effects of drugs such as barbiturates or benzodiazepines, electroconvulsive therapy, temporal lobe brain surgery, brain masses caused by tumors or infection, herpes encephalitis and other brain infections, depression, and sleep deprivation.

Conditions that can be treated via the methods of the invention therefore include cognitive disorders; neuro-degenerative disorders such as Alzheimer's disease; age-related dementias; age-induced memory impairment; drug-induced states including cocaine, amphetamine, alcohol-induced states; depression; attention deficit disorder; attention deficit hyperactivity disorder; psychosis; cognitive deficits associated with psychosis; and drug-induced psychosis.

Neurodegenerative diseases are a group of illnesses with diverse clinical importance and etiologies. Neurodegenerative diseases include motor neuron disease such as amyotrophic lateral sclerosis (ALS), cerebellar disorders, Parkinson's disease (PD), Huntington's disease (HD), cortical destructive Alzheimer's disease (AD) and schizophrenia. Numerous epidemiological and experimental studies provide risk factors for neurodegenerative diseases, for example, advanced age, genetic defects, abnormalities of antioxidant enzymes, excitotoxicity, cytoskeletal abnormalities, autoimmunity, mineral deficiencies, oxidative stress, metabolic toxicity, hypertension and other vascular disorders. Free radical toxicity, radical induced mutations and oxidative enzyme impairment and mitochondrial dysfunction due to congenital genetic defects also are associated with neurodegenerative diseases and other conditions of the central nervous system associated with cognitive impairment.

The methods provided by the invention can be useful for improving cognitive performance in subjects that suffer no chronic deficits. For example, the invention methods can be used to improve cognitive performance in a subject in any setting where bouts of sleep deprivation or exhaustion are routinely encountered, for example, a commercial setting such as the airline or health care industry; a military setting; or a recreational setting such as an endurance athletic event. The invention can be practiced to compensate for a decline in cognitive performance as is associated with temporary as well as prolonged sleep deprivation, mental exhaustion, physical exhaustion or over-exertion. For example, the method can be useful to increase cognitive performance in an athlete undergoing a peak performance or endurance event, for example, a long run such as, for example, a half-marathon, marathon or triathlon. Furthermore, the methods of the invention also can be useful to stimulate memory, both short term and long term, and learning ability in subjects that suffer no deficits, chronic deficits or temporary/acute deficits.

Cognitive performance of a subject is influenced by a variety of factors and the methods of the invention can be practiced to counteract any factors, for example, sleep deprivation that cause an impairment in cognitive performance. Adequate sleep sustains cognitive performance, while less than adequate sleep leads to a decrease in cognitive performance over time as described by Thorne et al., *Military Systems, Defense and Civil Institute of Environmental Medicine* (1983); Newhouse et al., *Neuropsychopharmacology* 2: 153-164 (1989); Newhouse et al., *Military Psychology* 4: 207-233 (1992), all of which are incorporated herein by reference in their entirety. Using computer-based cognitive performance tests, it has been shown that total sleep deprivation degrades human cognitive performance by approximately 25% for each successive period of 24 hours awake. Robust, cumulative decrements in cognitive performance occur during continuous total sleep deprivation as measured by computer-based testing and complex operational simulation. On fixed, restricted daily sleep amounts, cumulative reduced sleep also leads to a cognitive performance decline as described by Dinges et al., *Sleep* 20: 267-277 (1997), which is incorporated herein by reference. No other factor besides the amount of sleep contributes so substantially and consistently to the normal, daily variations in cognitive performance. Thus, the methods of the invention for improving cognitive performance can be useful in operational settings, both civilian and military, when sleep deprivation reduces productivity on cognitive tasks.

In addition to sleep/wake history, cognitive performance varies with the time of day. When humans follow a nocturnal sleep/diurnal wake schedule, for example, an 8-hour sleep/16-hour wake cycle, with nightly sleep commencing at approximately midnight, body temperature reaches a minimum usually between 2:00 AM and 6:00 AM. Body temperature then begins rising to a maximum usually between 8:00 PM and 10:00 PM. Likewise, systematic studies of daily human cognitive performance rhythms show that speed of responding improves across the day to reach a maximum in the evening, usually between 8:00 PM and 10:00 PM, then dropping more rapidly to a minimum occurring in the early morning hours, usually between 2:00 AM and 6:00 AM. Similar but somewhat less consistent rhythms have been shown from testing based on various cognitive performance tasks. Thus, superimposed on the effect of total sleep deprivation on cognitive performance there can be a variation in cognitive performance over each 24-hour period.

Various other factors have been shown to correlate with cognitive performance, including objective and subjective measures of sleepiness, drowsiness, and fatigue. For example, a relationship between excessive daytime sleepiness (EDS) and cognitive impairment has been reported by Ohayon and Vecchierini *Arch Intern Med.* 162: 201-208 (2002). Cognitive performance can be assessed by testing the performance on a wide variety of tasks, for example, vigilance tasks and tasks requiring sustained attention. For vigilance and other tasks, accuracy can be used as the measure of cognitive performance, while other tasks use reaction time or its inverse, speed. Still others use a measure that is calculated as speed multiplied by accuracy, that is the amount of useful work performed per unit of time. Those skilled in the art understand that vigilance tasks are appropriate measures of cognitive performance under conditions of sleep deprivation, and that either reaction time (speed) or some measure that takes reaction time into account is a valid and reliable way of measuring cognitive performance. These and other measures of cognitive performance known in the art can be useful to confirm improvement in cognitive performance by the invention methods.

The Multiple Sleep Latency Test (MSLT) is a widely accepted objective measure of sleepiness/alertness and can also be useful to predict or assess an impairment in cognitive performance. In the MSLT, individuals try to fall asleep while lying in a darkened, quiet bedroom. Various physiological measures used to determine sleep or wakefulness are recorded, for example, eye movements, brain activity and muscle tone, and the amount of time taken to reach the first 30 seconds of stage 1 (light) sleep is determined. Shorter latencies to stage 1 are considered to indicate greater sleepiness (lower alertness). Sleep latencies under 5 minutes are considered to be pathological and indicative of a sleep disorder or sleep deprivation. During both total and partial sleep deprivation, alertness and cognitive performance decline. Thus, there is a correlation between MSLT-determined sleepiness/alertness and cognitive performance, such that the MSLT as well as other tests known in the art for alertness as well as other features of cognitive performance, for example, can be useful to determine whether the application of the invention method for improving cognitive performance is indicated.

Subjective measures of alertness also have been shown to correlate with cognitive performance and can be used to predict cognitive performance impairments. As with the MSLT, during both total and partial sleep deprivation, scores on the Stanford Sleepiness Scale (SSS) increase. Similar to the MSLT, subjective tests such as the SSS-determined alertness can be used to predict or assess impairments in cognitive performance. Some other examples of subjective measures of sleepiness/alertness include the Epworth Sleepiness Scale as described by Johns, *Chest* 103: 30-36 (1993); the Karolinska Sleepiness scale as described by Akerstedt and Gillberg, *International Journal of Neuroscience* 52: 29-37 (1990). These and other tests known in the art that can be used to asses features of cognitive performance are useful to assess or predict an impairment in cognitive performance and to determine whether an indication exists to practice the methods provided by the invention.

In certain embodiments, the one or more flavonoid and/or antioxidant to be administered via a method of the invention can be obtained form a variety of sources. Flavonoids and antioxidants are readily available from commercial chemical suppliers ranging from 85-99% purity. Alternatively, as flavonoids and antioxidants are present in many naturally occurring substances, such as most plant species, the composition of the invention can comprise a flavonoid obtained from a naturally occurring source. For example, green tea leaves contain about 30% of flavonoids by weight. In particular, the flavonoid catechin and its gallate are major ingredients of green tea. Therefore, a pharmaceutical composition of the invention can comprise a flavonoid content derived from plants. Such plant-derived compositions can comprise extracts of plants or parts thereof which are processed in some way, for example, by fermentation. Thus, a plant-derived flavonoid or antioxidant includes aqueous or organic solvent extracts of plants or parts thereof. The plant material can be processed physically and/or chemically during production of the composition to extract flavonoids from the plant and so increase and enrich the flavonoid content of the composition.

Plant materials containing flavonoids and/or antioxidants can be fractionated along or in combination with these other plants known to be high in the various flavonoids. The fractionation results in substantially removing water, carbohydrates, proteins, and lipids from the source maternal. Fractionation methods are well known in the art and described, for example, in U.S. Pat. Nos. 5,702,752; 4,428,876. It is also understood that an extraction using ethyl acetate or n-butanol can be used as described in U.S. Pat. No. 5,702,752. Other extraction processes, which can be used alone or in combination, include differential solubility, distillation, solvent extraction, adsorptive means, differential molecular filtration and precipitation.

Compositions containing as active ingredient one or more flavonoids and/or one or more antioxidants can be prepared by known procedures using well-known and readily available ingredients. The one or more flavonoids and/or one or more antioxidants administered to a physically active subject, for example, a subject undergoing a physical exercise routine, in the methods of the invention for improving cognitive performance or enhancing neurogenesis can be administered in combination with a pharmaceutically acceptable carrier.

In making a pharmaceutical composition containing as active ingredient one or more flavonoids and/or one or more antioxidants, the active ingredient can be mixed with a carrier, or diluted by a carrier, or enclosed within a carrier, and can be in the form of a capsule, sachet, paper, or other container. When the carrier serves as a diluent, it can be a solid, semisolid, or liquid material that acts as a vehicle, excipient, or medium for the active ingredient. The pharmaceutical compositions can be in the form of food bars, tablets, pills, powders, lozenges, sachets, cachets, elixirs, suspensions, emulsions, solutions, syrups, aerosols, ointments containing, for example, up to 2% or more, 5% or more, 7% or more, 10% or more, by weight of active ingredient, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragcanth, gelatin, calcium silicate, micro-crystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention can be formulated so as to provide quick, sustained, or delayed release of the active ingredient after administration to the subject by employing procedures well known in the art.

The pharmaceutical compositions containing as active ingredient one or more flavanoids and/or one or more antioxidants can be formulated in a unit dosage form, each dosage containing from about 1 mg to about 500 mg, more preferably about 5 mg to about 300 mg, for example, 25 mg, 30 mg, 35 mg, 40 mg, 50 mg, 100 mg or more, of the active ingredient. A unit dosage form can be a physically discrete unit suitable as unitary dosages for human subjects and other mammals, each unit containing a predetermined quantity of active material calculated to produce the desired therapeutic effect, in association with a suitable pharmaceutical carrier, diluent, or excipient.

The particular dose of active ingredient, in particular, of one or more flavanoids and/or one or more antioxidants, to be administered according to this invention can be determined by the particular circumstances surrounding the case, including the compound administered, the route of administration, the particular condition being treated, and similar considerations. For example, the dose for a subject suffering from a neurodegenerative condition associated with cognitive impairment can depend on factors such as the severity of the impairment, chronic vs. acute phase of the condition, as well as other therapies that are being administered. On the other hand, a less individualized dosing also can be appropriate, for example, where the subject is an otherwise healthy individual and the cognitive impairment is due to fatigue or sleep deprivation a prepackaged unit containing the active ingredients in a food bar format can be useful.

Moreover, the one or more flavonoids or one or more antioxidants can be administered in combination with any number of further components, such as those typically used in the food industry and/or in the pharmaceutical industry. Such components can include nutrients, for example, trace elements and vitamins, antioxidants, therapeutic substances, especially those having a therapeutic effect in relation to conditions affecting the central nervous system, flavoring, and sweeteners, including artificial sweeteners, such as aspartame.

Examples of the above include carotenoids such as lutein, lycopene, or alpha- and/or beta-carotene; antioxidant nutrients or anti-inflammatory agents such as vitamin A, vitamin C, vitamin E(alpha-tocopherol and other active tocopherols), folic acid, selenium, copper, zinc, manganese, ubiquinone (coenzyme Q10), salicylic acid, 2,3-dihydroxy benzoic acid, and 2,5-dihydroxy benzoic acid. Antioxidants such as carotenoids and vitamin E are partially destroyed in the gastrointestinal tract by oxidation. By inclusion of these compounds in the composition of the invention it is believed that this process is inhibited and more antioxidants are absorbed.

It is understood that a composition containing of one or more flavanoids and/or one or more antioxidants, to be administered according to this invention can be administered by a variety of routes including oral, rectal, transdermal, subcutaneous, intravenous, intramuscular, or intranasal routes. Alternatively, the pharmaceutical composition can be administered by continuous infusion. For example, for oral administration to a human subject 100 mg, 200 mg, 300 mg, 400 mg, 500 mg, 600 mg, 700 mg, 800 mg, 900 mg or more can be an appropriate dose, while intravenous administration can be at a dose of 5 mg/kg or more, 7 mg/kg or more, 10 mg/kg or more, 15 mg/per kg or more. A typical daily dose can contain from about 0.01 mg/kg to about 100 mg/kg of the active compound of this invention. Preferably, daily doses will be about 0.05 mg/kg to about 50 mg/kg, more preferably from about 0.1 mg/kg to about 25 mg/kg.

As described above, the methods provided by the invention can enhance neurogenesis and improve an impairment cognitive performance associated with a condition of the central nervous system, for example, Alzheimer's Disease, Parkinson's Disease, Huntington's Chorea, senile dementia, Pick's disease, parkinsonism dementia syndrome, progressive subcortical gliosis, progressive supranuclear palsy, thalamic degeneration syndrome, hereditary aphasia, myoclonus epilepsy, sleep deprivation, depression, stroke, ischemia and brain trauma.

The term "effective amount" refers to the amount or dose of the compound which provides the desired effect in the subject to whom it is administered.

As used in reference to cognitive performance, the term is intended to mean an amount sufficient to improve cognitive performance or reduce the severity of an impairment in cognitive performance in a subject compared to a subject that is not administered the amount. Reduction in severity encompasses preventing, restraining, slowing, stopping, or reversing progression, severity, or a resultant symptom, including behavioral or physiological indicators, biochemical markers or metabolic indicators. Symptoms of impairment in cognitive performance include, for example, reduced mental functions, including learning, problem solving, remote memory, recent memory, word comprehension, orientation, attention span, calculation, abstract thinking, and judgment. A reduction in severity also includes a delay in the onset of symptoms in a subject susceptible to impairment of cognitive performance.

As used in reference to neurogenesis, the term "effective amount" is intended to mean an amount sufficient to increase the rate of cell genesis in the central nervous system; to increase the rate of cell survival, to increase the proportion of cells with a neuronal or glial phenotype that develop from the precursor population or to reduce the severity of an impairment associated with neuronal degeneration performance in a subject compared to a subject that is not administered the amount. Cell genesis can be assessed by quantitating the number of dividing cells by methods well known in the art. Detection of cell genesis by determination of brain volume changes can be accomplished by a variety of imaging methods known in the art, for example computerized tomography (CT), magnetic resonance (MR), single photon emission computed tomography (SPECT) and magnetoencephalography (MEG) to scan the central nervous system. In addition, electro-encephalograms and evoked potentials could be used to measure changes in brain activity and plasticity. Moreover, lumbar puncture or spinal tap procedures can be used to draw out cerebrospinal fluid, which can be tested for biochemical markers indicative of cell proliferation, survival, phenotype or integrity. These neuroimaging, biochemical and other methods well known in the art can be used to determine neurogenesis.

An amount effective to achieve a desired result in a human subject can be extrapolated from an animal model, taking into account and making adjustments for art-known pharmacokinetic differences in absorption, distribution, metabolism, and elimination. Furthermore, to determine an effective amount for administration pharmacodynamic differences, for example, biological ligands or other targets that impact the biological response also can be taken into account. It is known in the art how to use mathematical models to identify the daily intake resulting in a target tissue concentration equivalent to the target tissue concentration in the experimental animal that was associated with the observed response. In addition, it is understood that the estimated animal intake associated with the observed response can be extrapolated to a human intake using an appropriate allometric relationship.

As used herein, when used in reference to a subject, the phrase "physically active" refers to a subject that has the metabolic, cellular, physiological and biochemical characteristics that result from physical activity. Generally, the term refers to a subject that undergoes a physical exercise routine, for example, a regular aerobic workout regimen. In general, it is contemplated that within the same time period in which the one or more flavonoids and/or one or more antioxidants are administered, the subject undergoes a routine of limited exercise, mild to moderate exercise, or strenuous exercise. It is not necessary for the exercise routine to be regular as long as sufficient metabolic, cellular, physiological and biochemical characteristics of physical activity, for example, increased metabolic rate, blood flow, cellular respiration, are attained to result in a synergistic effect when combined with the administration of an effective amount of one or more flavonoids and/or one or more antioxidants.

Furthermore, the administration of the one or more flavonoids and/or one or more antioxidants can take place before, during, or after the exercise routine is being performed. It is understood that the administration does not have to take place while the subject is exercising. Instead, the administration can be performed within any time frame vis-à-vis the physical exercise routine that is determined to be of sufficient temporal proximity to achieve the synergistic effect that results from the exercise and the administration of an effective amount of the one or more flavonoids and/or one or more antioxidants. A mild to moderate exercise is one where approximately 50% to 70% of the subject's maximum heart rate is reached. For humans, the maximum heart rate is generally calculated by subtracting the individual's age from 220. If desired, a strenuous exercise regimen can be pursued where the subject reaches 80% or more of the subject's maximum heart rate.

Any amount of physical exercise routine sufficient to achieve an improvement in cognitive performance or enhancement of neurogenesis when incorporated into a method of the invention is contemplated. Similarly, a subject in which the metabolic, cellular, physiological and biochemical characteristics of physical activity, for example, increased metabolic rate, blood flow, cellular respiration, are attained in the absence of physical exercise, but nevertheless sufficiently to result in a synergistic effect when combined with the administration of an effective amount of one or more flavonoids and/or one or more antioxidants is considered a physically active subject as contemplated by the invention.

It is understood that modifications which do not substantially affect the activity of the various embodiments of this invention are also provided within the definition of the invention provided herein. Accordingly, the following examples are intended to illustrate but not limit the present invention.

EXAMPLE I

Administration of Either a Flavonoid or an Antioxidant Improves in Cognitive Performance in Subjects that Exercise This example describes that administration of either 3'- and 4'-methylated epicatechin (1:1) or N-tert-Butyl-phenylnitrone (PBN) enhances spatial memory performance in mice that exercise.

Figure 4:
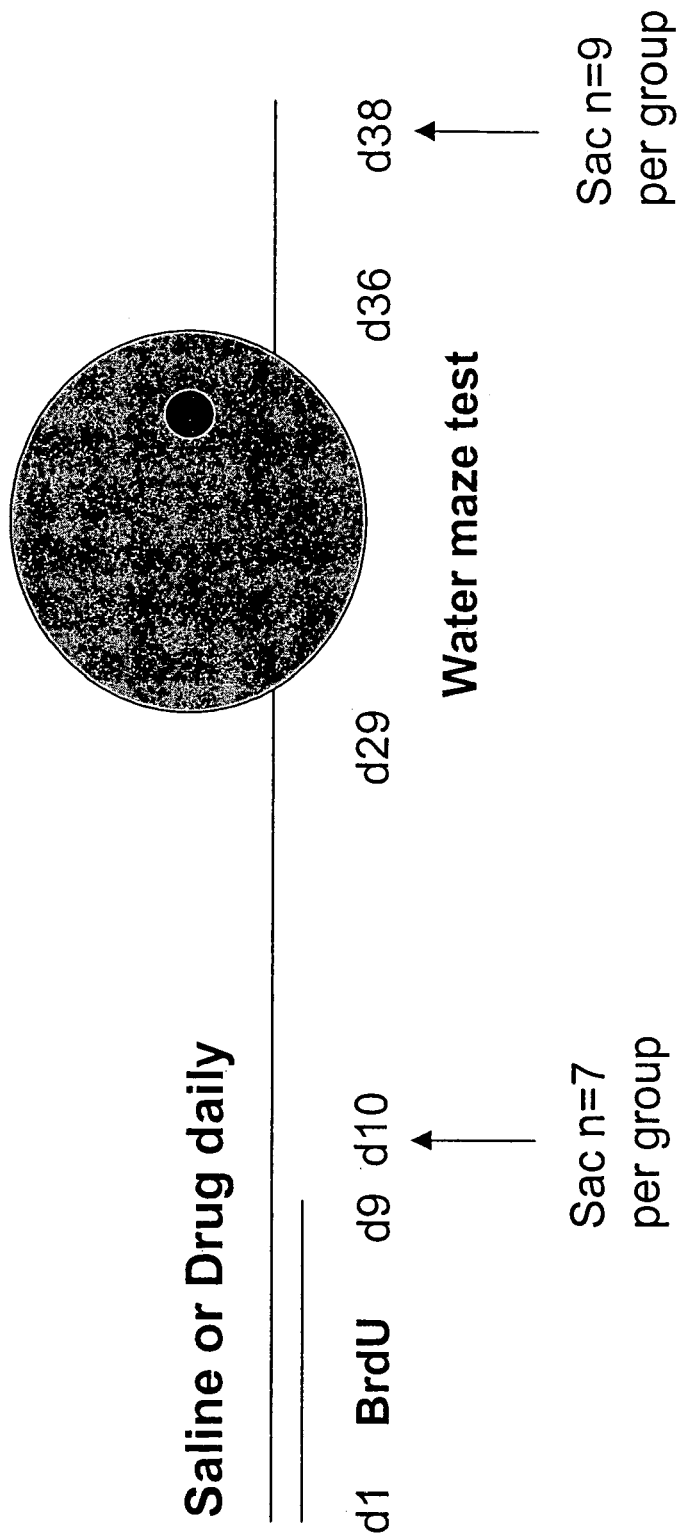
FIG. 4 shows a diagram of the study design.

Ninety-six female C57BL/6 mice, ten weeks old were purchased from Harlan SD and housed individually with a reversed day/night cycle: lights on at 10 p.m. and off at 10 a.m. The mice were divided into six groups of 16 mice each: Control/Saline (CS) Control/PBN (CP), Control/Mars (CM), Runner/Saline (RS), Runner/PBN (RP) and Runner/Mars (RM). Runners were moved into a cage with a running wheel (Lafayette Instruments) for 4 hours per day, from 10 a.m. to 2 p.m. The mice received daily injections of saline, N-tert-Butyl-phenylnitrone (PBN, 30 mg/kg) or 3'- and 4'-methylated epicatechin 1:1 (Mars, 20 mg/kg). A diagram version of the study design is set forth in FIG. 4.

Figure 2:
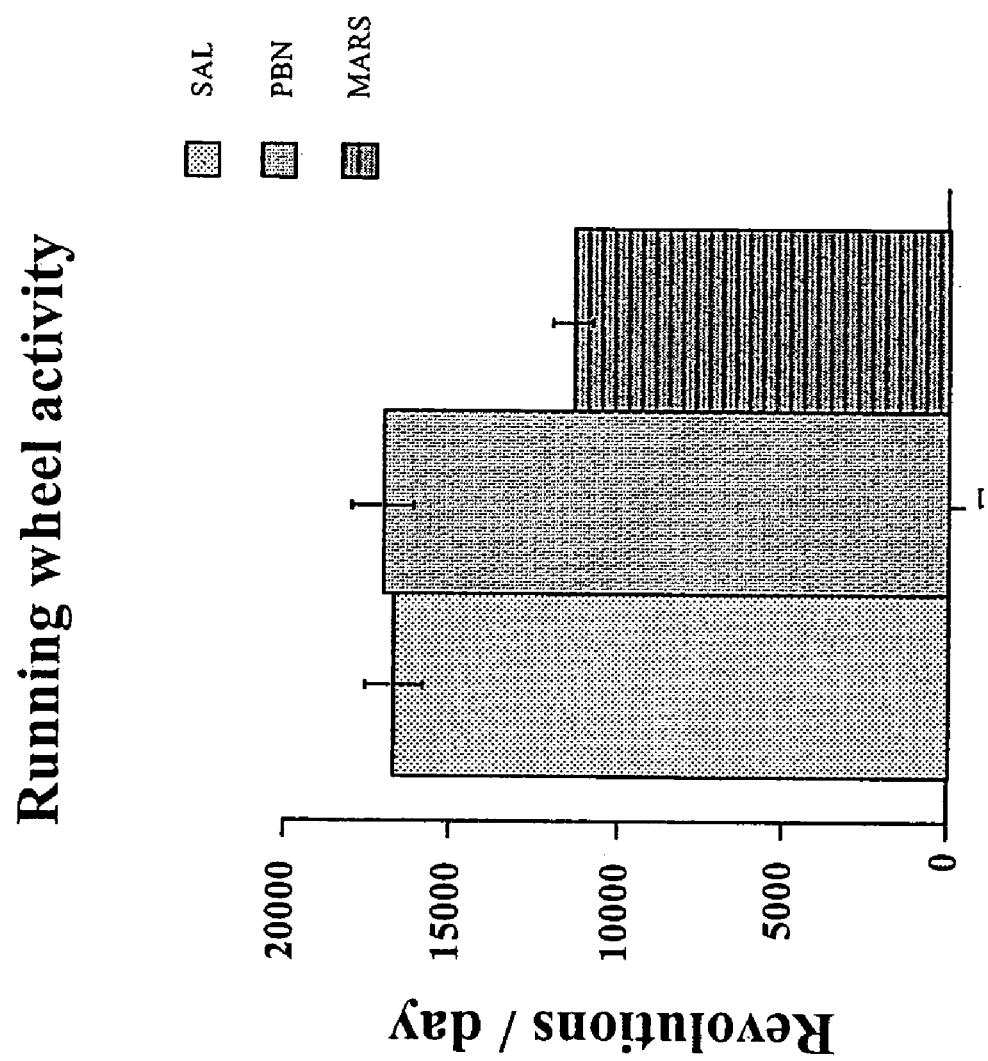
FIG. 2 shows the differences the running wheel activity between the S, PBN and M groups.

Mice in the running groups were placed in cages with wheels after drug injection for about 4 hours daily. The number of wheel revolutions differed significantly between the groups ($F(2,24)=13.9$, $p<0.0001$). Specific comparisons showed the RM animals ran significantly less than the RS or RP mice ($p<0.0001$). As shown in FIG. 2, there was no difference between RS and RP ($p>0.96$).

During the first nine days animals also received daily intraperitoneal BrdU injections (Sigma, St. Louis, Mo.); dissolved in 0.9% NaCl, filtered sterile at 0.2 μm, 50 μg/g body weight at 10 mg/ml) to label dividing cells.

On day 10, 7 animals from each group were given an overdose of anesthetics and perfused transcardially with cold 4% paraformaldehyde in 0.1 M PBS to study the effect of the drugs on cell proliferation. The remaining animals, 9 per group (except for CM in which one mouse died, n=8) continued in their respective conditions for 28 days and were tested in the water maze between days 29-36. On day 38 the remaining mice were perfused.

Spatial Learning

To assess spatial learning the mice were trained with two trials per day over eight days on the Morris water maze as described by Morris, *J. Neurosci. Methods* 11: 47-60 (1984), which is incorporated herein by reference in its entirety. The platform was hidden 1 cm below the surface of water, made opaque with white non-toxic paint. The starting points were changed every day. Each trial lasted either until the mouse had found the platform or for a maximum of 40 seconds. All mice were allowed to rest on the platform for 10 seconds at the end of each trial. The latency to the platform, length of swim path and swim speed was recorded semi-automatically by a video tracking system (Ethovision, Noldus).

Figure 1B:
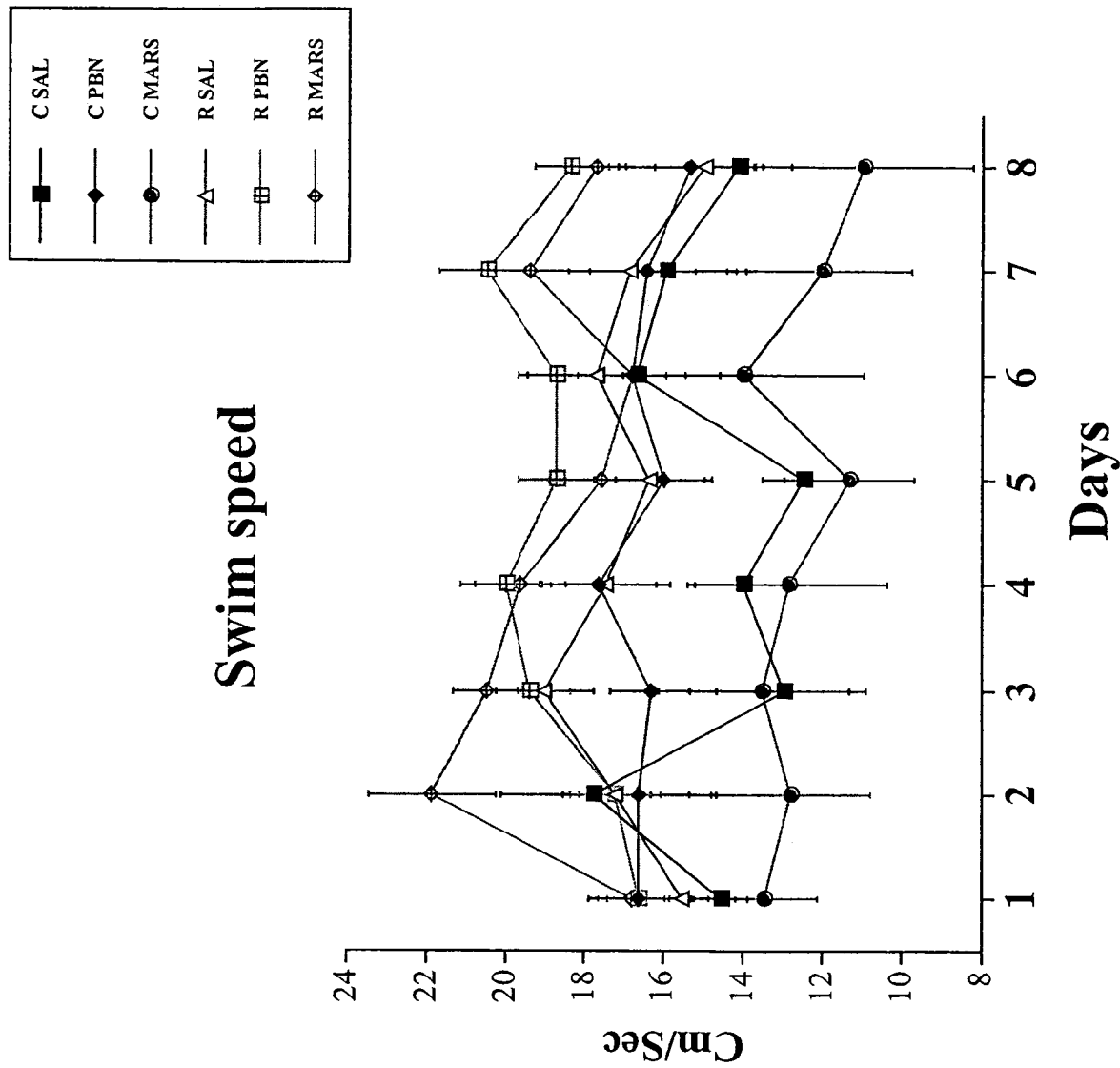

To assess memory function mice were trained in the water maze for 8 days with 2 trials per day between days 29-36 of the experiment. ANOVA with repeated measures (Days) showed that there was a significant difference between the groups in latency ($F(5,47)=2.62$, $p<0.04$) to the platform as is shown in FIG. 1A. Specific comparisons (Fischer's PLSD) showed that RM mice reached the platform sooner than all other groups except for RP ($p<0.05$). Analysis of variance per day indicated that RM animals showed enhanced performance from the first day of testing whereas RP mice had significantly shorter latencies from day 6 onwards. However, when measuring swim speed, there was also a significant difference between the groups ($F(5,47)=3.37$, $p<0.01$), raising the possibility that the RM and RP animals performed better due enhanced motor rather than cognitive skills. As shown in FIG. 1B, specific comparisons showed the RS, RM and RP mice swam faster than CS and CM animals ($p<0.03$). There was no difference between the runners and CP. CP was significantly faster than CM ($p<0.05$).

To further investigate whether the RM and RP had improved learning, the swimming distance was analyzed for all trials. There was no significant difference between the groups in an overall analysis ($F(5,47)=1.55$, $p=0.19$). Subsequently, only the trials in which the animals found the platform were included whereas the trials where the animals that did not find the platform were given a cut-off score of 715 cm, which corresponds to the average swim distance over 40 seconds when no platform is present.

Figure 1C:
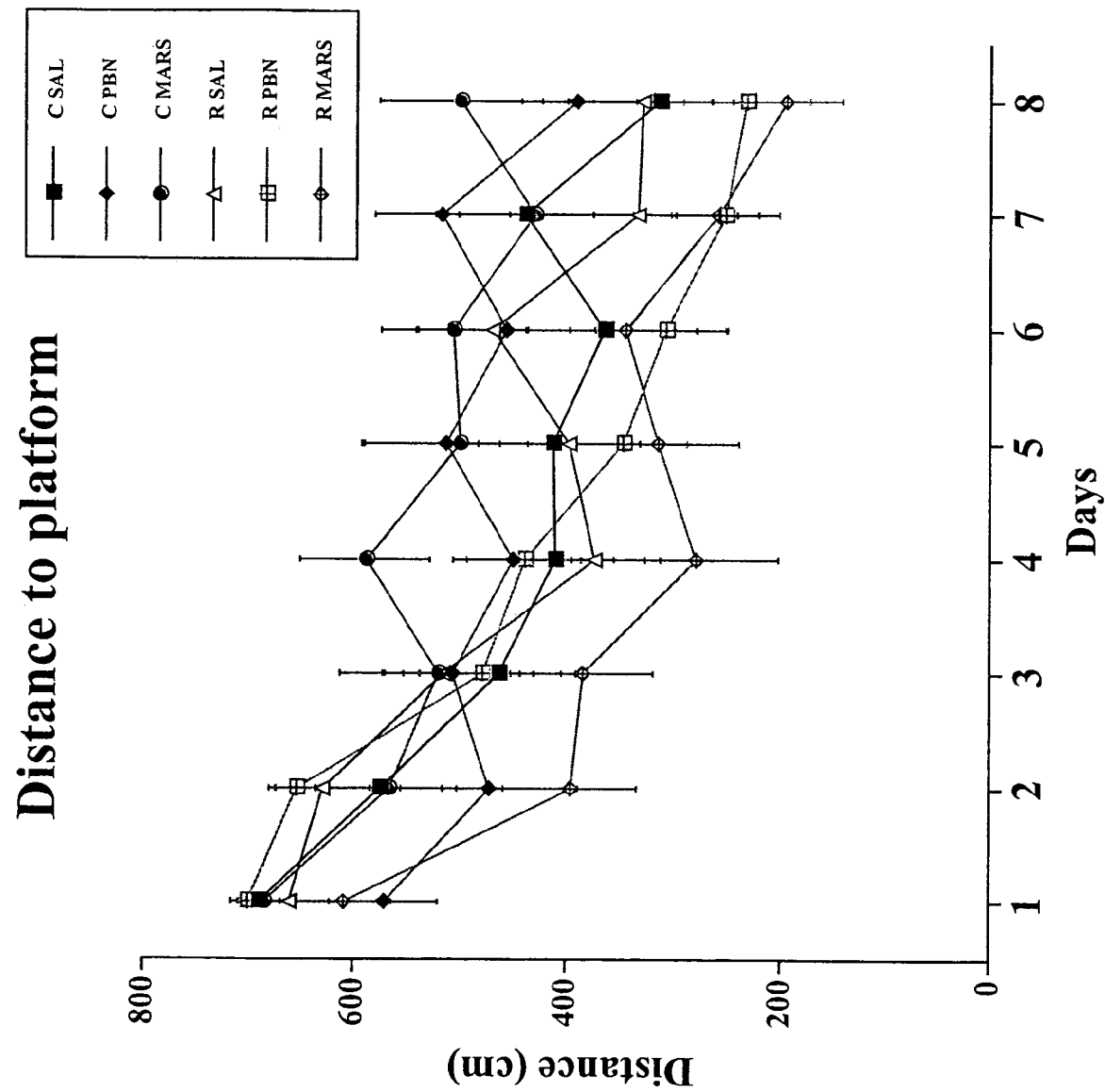

Using this analysis there was a significant difference in path length between the groups ($F(5,47)=2.7$, $p<0.03$). In particular, as shown in FIG. 1C, specific comparisons showed that the RM mice traveled significantly shorter distances to the platform as compared to all the other groups except for RP ($p<0.05$).

Taken together these findings indicate that the Mars compound enhances spatial memory performance in mice that exercise (FIG. 1).

EXAMPLE II

Administration of Either a Flavonoid or an Antioxidant Enhances Neurogenesis in Subjects that Exercise This example describes that administration of either 3'- and 4'-methylated epicatechin (1:1) or N-tert-Butyl-phenylnitrone (PBN) enhances neurogenesis in mice that exercise.

RM animals have more cell proliferation than the RS mice, a finding that correlates with the enhanced learning observed in the RM and RP groups.

To confirm neurogenesis, immunohistochemistry for BrdU was performed on a 1:6 series of free-floating 40-μm coronal sections that were pretreated for BrdU immunohistochemistry by denaturing DNA, as described previously by van Praag et al., *Procl. Natl. Acad. Sci. USA* 96: 13427-13431 (1999), which is incorporated herein by reference in its entirety. The antibody used was mouse anti-BrdU (Boehringer Mannheim, Indianapolis, Ind.) 1:400. To visualize the BrdU-labeled cells, staining for BrdU with the peroxidase method was used (ABC system, with biotinylated donkey anti-mouse antibodies and diaminobenzadine as chromogen; Vector Laboratories, Burlingame, Calif.). Cells were counted at 40× using an upright brightfield microscope (Olympus).

Cell Proliferation in the Dentate Gyrus

Figure 3:
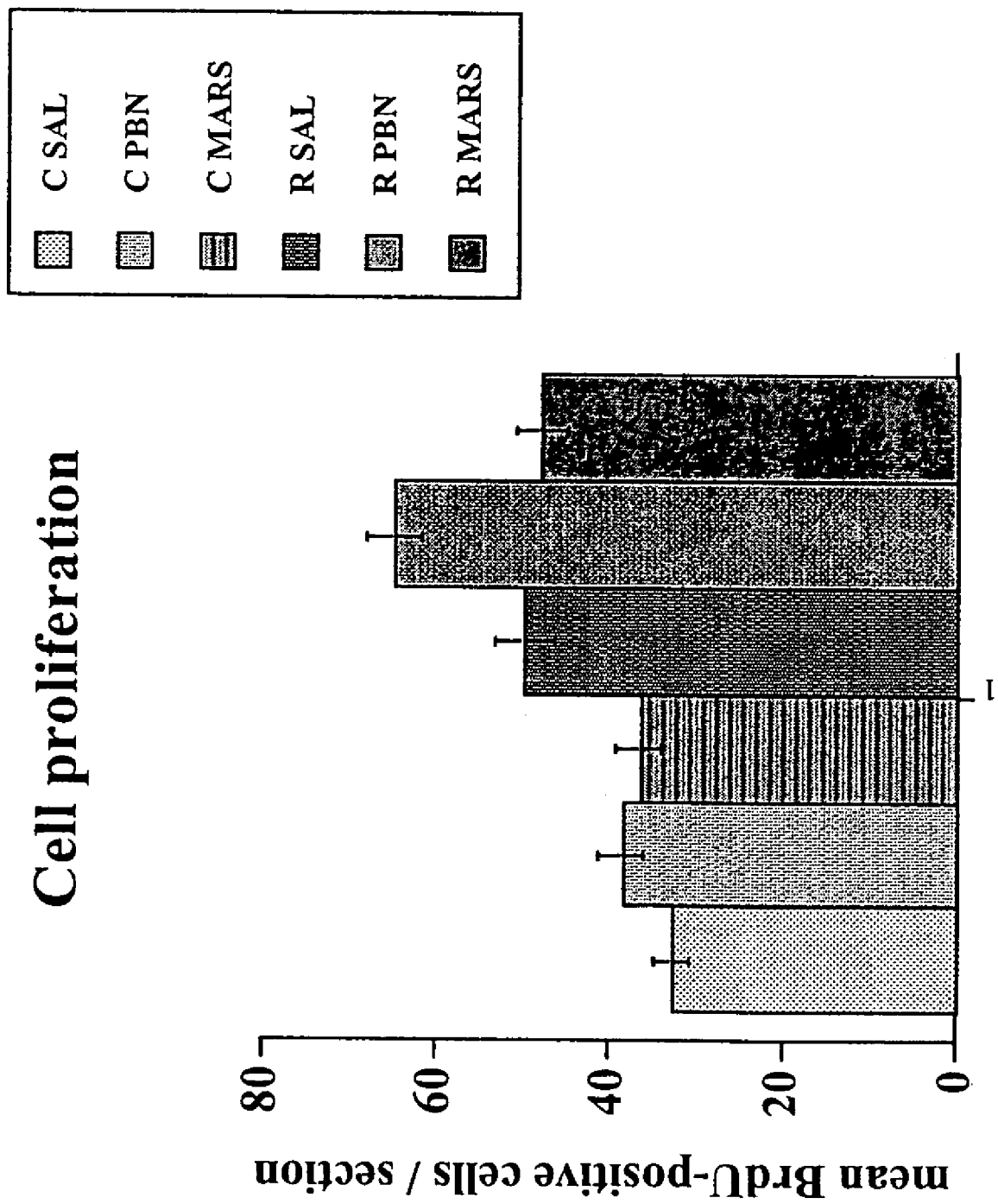
FIG. 3 shows a histogram of the cell genesis data. BrdU-positive cell numbers determined at the early time point (day 10) show that cell genesis is enhanced by running.

BrdU-positive cells were analyzed in mice that were allowed to survive for the first 10 days of the experiment. At this time point cell proliferation, but not neurogenesis can be assessed, since it takes about a month for a newly born cell to become a neuron (van Praag et al., *Nature* 415: 1030-1034 (2002), which is incorporated herein by reference in its entirety). The average number of BrdU-labeled cells per section was significantly greater in Runners than in Controls ($F(5,36)=6.44$, $p<0.0002$) (FIG. 3). As shown in FIG. 3, the greatest increase was observed in the RP mice. Specific comparisons showed that there was more cell genesis in these animals than in all the other groups (p<0.03). The RM mice only show more cell proliferation than CS (p<0.03), whereas the RS animals had more cell genesis than both CS and CM mice.

A positive correlation exists between the amount of running and the number of cells produced as described by Allen et al., *Genes & Development* 15: 554-566 (2001); Rhodes et al., *Behavioural Neuroscience* (2003), both of which are incorporated herein by reference in their entirety.

As set forth above the RM mice run less than RS and RP animals. However, if the number of wheel revolutions per day is equalized among the groups it can be expected that the RM animals have more cell proliferation than the RS mice, a finding that correlates with the enhanced learning observed in the RM and RP groups (FIG. 1).

Cell Survival and Neurogenesis in the Dentate Gyrus

We are currently processing the tissue of the animals that survived for 38 days to assess the effects of the drugs and exercise on the number of newborn neurons. Cell survival of neurons visualized by BrdU-labeling as described above, indicated that a significantly higher amount of neuronal cell survival between in the R compared to the S groups. To further test the differences between the RS, RM and RPBN groups, further studies will be performed that take into account and normalize for the difference in running activity between these groups. It is expected that, one normalized, the RM group will show a significant increase in neuronal cell survival.

Throughout this application various publications have been referenced. The disclosures of these publications, each in its entirety, are hereby incorporated by reference in this application in order to more fully describe the state of the art to which this invention pertains. Although the invention has been described with reference to the examples provided above, it should be understood that various modifications can be made without departing from the spirit of the invention.

We claim:

1. A method for improving cognitive performance in a mammal comprising administering to a physically active mammal in need thereof an effective amount of a composition comprising a compound having the formula

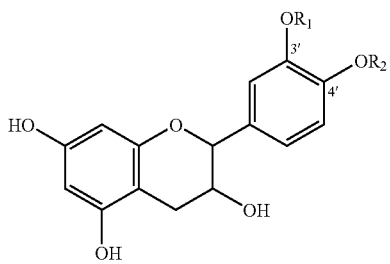

wherein the composition comprises a compound wherein R1 is —CH$_3$ and wherein R2 is —H and a compound wherein R2 is —CH$_3$ and wherein R1 is —H; or
wherein the composition comprises a compound wherein R1 and R2 is —CH$_3$.

2. The method of claim 1, wherein the composition comprises 3'-4'-O-methyl epicatechin.

3. The method of claim 1, wherein the composition comprises 3'-O-methyl epicatechin and 4'-O-methyl epicatechin.

4. The method of claim 1, wherein said mammal is undergoing a physical exercise routine.

5. The method of claim 1, wherein the mammal undergoes a routine of exercise within the same time period in which the compound is administered.

6. The method of claim 1, wherein said mammal is a human.

7. The method of claim 1, wherein said mammal is afflicted with a condition of the central nervous system.

8. The method of claim 7, wherein the mammal is a human suffering from Huntington's Chorea, senile dementia, Pick's disease, progressive subcortical gliosis, progressive supranuclear palsy, thalamic degeneration syndrome, hereditary aphasia, myoclonus epilepsy, depression, stroke, or ischemia.

9. The method of claim 7, wherein the mammal is a human suffering from brain trauma.

10. The method of claim 7, wherein the mammal is a human suffering from Alzheimer's Disease, parkinsonism dementia syndrome, or Parkinson's Disease.

11. The method of claim 7, wherein the mammal is a human suffering from a drug induced state.

12. The method of claim 11, wherein the drug induced state comprises a cocaine, amphetamine, barbiturate, benzodiazepine, or alcohol-induced state.

13. The method of claim 6, wherein the human is afflicted with alcoholism.

14. The method of claim 6, wherein the human suffers from sleep deprivation and/or exhaustion.

15. The method of claim 14, wherein the human works in the airline industry or health care industry.

16. The method of claim 14, wherein the human is in the military.

17. The method of claim 6, wherein the human is an endurance athlete.

18. The method of claim 14, wherein the composition comprises 3'-O-methyl epicatechin and 4'-O-methyl epicatechin.

19. The method of claim 14, wherein the composition comprises 3'-O-methyl epicatechin.

20. The method of claim 16, wherein the composition comprises 3'-O-methyl epicatechin and 4'-O-methyl epicatechin.

21. The method of claim 16, wherein the composition comprises 3'-4'-O-methyl epicatechin.

22. A method for stimulating neurogenesis comprising administering to a physically active mammal in need thereof an effective amount of a composition comprising a compound having the formula

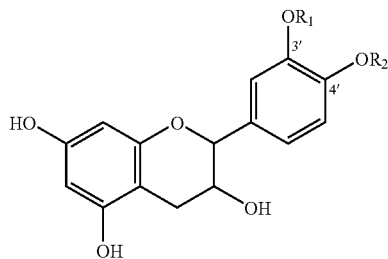

wherein the composition comprises a compound wherein R1 is —CH$_3$ and wherein R2 is —H and a compound wherein R2 is —CH$_3$ and wherein R1 is —H; or
wherein the composition comprises a compound wherein R1 and R2 is —CH$_3$.

23. The method of claim 22, wherein the composition comprises 3'-4'-O-methyl epicatechin.

24. The method of claim 22, wherein the composition comprises 3'-O-methyl epicatechin and 4'-O-methyl epicatechin.

25. The method of claim 22, wherein said subject is undergoing a physical exercise routine.

26. The method of claim 25, wherein the mammal undergoes a routine of exercise within the same time period in which the compound is administered.

27. The method of claim 22, further comprising administration of a pharmaceutically acceptable carrier.

28. The method of claim 22, wherein said mammal is a human.

29. The method of claim 22, wherein said mammal is afflicted with a condition of the central nervous system.

30. The method of claim 29, wherein the mammal is a human suffering from Huntington's Chorea, senile dementia, Pick's disease, progressive subcortical gliosis, progressive supranuclear palsy, thalamic degeneration syndrome, hereditary aphasia, myoclonus epilepsy, depression, stroke, or ischemia.

31. The method of claim 29, wherein the mammal is a human suffering from brain trauma.

32. The method of claim 29, wherein the mammal is a human suffering from Alzheimer's Disease, parkinsonism dementia syndrome, or Parkinson's Disease.

33. The method of claim 28, wherein the mammal is a human suffering from a drug induced state.

34. The method of claim 33, wherein the drug induced state comprises a cocaine, amphetamine, barbiturate, benzodiazepine, or alcohol-induced state.

35. The method of claim 28, wherein the human is afflicted with alcoholism.

36. The method of claim 28, wherein the human suffers from sleep deprivation and/or exhaustion.

37. The method of claim 36, wherein the human works in the airline industry or health care industry.

38. The method of claim 36, wherein the human is in the military.

39. The method of claim 28, wherein the human is an endurance athlete.

40. The method of claim 36, wherein the composition comprises 3'-O-methyl epicatechin and 4'-O-methyl epicatechin.

41. The method of claim 36, wherein the composition comprises 3'-4'-O-methyl epicatechin.

42. The method of claim 38, wherein the composition comprises 3'-O-methyl epicatechin and 4'-O-methyl epicatechin.

43. The method of claim 38, wherein the composition comprises 3'-4'-O-methyl epicatechin.

* * * * *